United States Patent [19]

Maltagliati

[11] Patent Number: Plant 6,908

[45] Date of Patent: Jul. 11, 1989

[54] ROSE PLANT — MALNINO VARIETY

[75] Inventor: Mark Maltagliati, Richmond, Calif.

[73] Assignee: Ninomiya Nursery Co., Richmond, Calif.

[21] Appl. No.: 191,116

[22] Filed: May 6, 1988

[51] Int. Cl.[4] ..... A01H 5/00
[52] U.S. Cl. ..... Plt./14
[58] Field of Search ..... Plt./14

*Primary Examiner*—Robert E. Bagwill

*Attorney, Agent, or Firm*—Burns, Doane, Swecker & Mathis

[57] ABSTRACT

A new and distinct variety of Grandiflora rose plant is provided which forms attractive long lasting pure white double blossoms generally one per stem. The new variety reflowers well and can be grown to advantage in a garden or for the production of cut flowers. The new variety came into being as a sport of the Lifirane variety which itself is a sport of the Sonia variety.

1 Drawing Sheet

SUMMARY OF THE INVENTION

The new variety originated as a sport of a rose plant of the Lifirane variety U.S. Plant Pat. No. 4,034. The Lifirane variety is a sport of the Sonia variety U.S. Plant Pat. No. 3,095. The Sonia variety sometimes is known as the Sweet Promise variety. The new sport of the present invention occurred spontaneously and was of unknown causation. More specifically, the new variety was discovered by me in September 1984 on a planting of the Lifirane variety made in greenhouses of the Ninomiya Nursery Co. at Richmond, Calif. during the spring of 1984. The new variety was discovered as a pure white sport growing from a single eye of a plant of the Lifirane variety which from all other points produced the characteristic rose neyron blossoms of the Lifirane variety. I marked the plant for continuing observation, and after successive reblooms the stability of the sport was apparent. The stable nature of the new variety has been fully confirmed over the following years both on the original plant and in subsequent generations following asexual propagation.

From the physical point of view the new variety generally corresponds to the Lifirane variety with the exception of its distinctive pure white blossom coloration.

It was found that the new variety of Grandiflora rose plant of the present invention possesses the following combination of characteristics:

(a) exhibits and erect growth habit,
(b) forms fully double pure white blossoms which generally are borne one per stem and are long lasting on or off the plant,
(c) forms vigorous vegetation, and
(d) exhibits very good resistance to diseases.

The new variety well meets the needs of the floriculture industry. It can be grown in gardens or under glass for the production of attractive cut flowers.

The new variety undergoes asexual propagation by a number of routes, including T-budding onto an understock of *Rosa manettii,* etc. The characteristics of the new variety have been found to be strictly transmissible by such asexual propagation from one generation to another.

The new variety has been named the Malnino variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were grafted on *Rosa manettii* understock and were grown in a greenhouse at Richmond, Calif.

At the top are shown two segments of floral stems. At the left are shown a specimen of a leaf with seven leaflets—plan view—obverse, a specimen of a leaf with five leaflets—plan view—reverse, and a specimen of a leaf with three leaflets—plan view—obverse. At the bottom is shown a leaf with five leaflets—plan view—obverse. At the left center is shown a floral bud at the opening of the petals. At the upper right is shown a pair of flowers in the course of opening—plan view—obverse. At the far right is shown floral bud before the opening of the sepals. To the left of the floral bud is shown a young shoot. At the right center is shown a specimen of a fully open flower—plan view—obverse.

DETAILED DESCRIPTION

The chart used in the identification of the colors is that of the Royal Horticultural Society (R.H.S. Colour Chart). The description is based on plants made during July while grafted on *Rosa manettii* understock and growing in a greenhouse at Richmond, Calif. The coloration in common terms precedes reference to the chart.

Class: Grandiflora.

Plant:

*Height.*—The length of the flowering stem commonly averages 50 to 70 cm. as with the Lifirane variety when the plant is cut to a height of 85 cm.

*Habit.*—Erect.

Branches:

*Color.*—Young stems: lettuce green, Yellow-Green Group 144B. Adult wood: spinach green, Yellow-Green Group 146B.

Leaves:

*Stipules.*—Adnate, pectinate, long (commonly ⅔ of the petiole), sometimes fairly wide.

*Petioles.*—Upper surface: grooved, light green on young leaves with a groove which is lightly tinted red, and light green or adult foliage with slightly glandular edges. Under surface: light green sometimes with small hooked thorns.

*Leaflets.*—Number: 3, 5 (most often), and 7. Shape: elliptical with a pointed tip. Serration: simple and regular. Texture: leathery. General appearance: dull foliage, fairly ample and relatively dense, similar to that of the Lifirane variety. Color (young foliage): upper surface: light green, Green Group 137C. The central vein and the teeth of the edges of the petioles and leaves are tinted with red. Under surface: green, Green Group 138B, more or less tinted with reddish coloration on the periphery. Color (adult foliage): upper surface: medium green, Green Group 137A. Under surface: greyish green, Greyish-Green Group 191B.

Inflorescence:

*Number of flowers.*—Generally one flower per stem.

*Peduncle.*—Light green, fairly rigid. The length is approximately 8 to 10 cm. on average.

*Sepals.*—Upper surface: normal, light green in coloration. Under surface: hairy and whitish, the average length commonly is approximately 28 mm., and the average width commonly is approximately 9 mm.

*Buds.*—Shape: elongated and slightly cylindrical. Length: when the sepals open approximately 2.5 cm. outside the calyx. Size: medium. Color upon opening: upper surface: white with a greenish tinge, Green-White Group 157B. under surface: white with a greenish tinge, Green-White Group 157A.

*Flower.*—Shape: double. Diameter: when fully open approximately 10 cm. on average. Color (when opening): upper surface: white, White Group 155A. under surface: white, White Group 155A. Under surface: white, Green-White Group 157B, with a yellowish area at the base of the petal. Color (when blooming): upper surface: white, White Group 155A. Under surface: white, White Group 155B. Color (at end of opening): upper surface: white, White Group 155. Under surface: white, White Group 155A, with an area of yellowish coloration at the base of the petal. Fragrance: very light. Lasting quality: long when cut or on the plant. Petal number: approximately 50 to 55 on average commonly including approximately 45 true petals and 5 to 10 partially formed petals at the center. Petal form: broadly rounded. Texture: consistent. Petal drop: the petals drop off clearly. Stamen number: approximately 100 on average. Anthers: normal in length and yellow in coloration. Filaments: irregular in length and yellowish-green in coloration. Pistils: approximately 60 on average. Stigmas: whitish. Styles: fuschia in coloration. Receptacle: light green and smooth.

Development:

*Vegetation.*—Very vigorous.

*Blooming.*—Exhibits and excellent reblooming capacity.

*Aptitude to bear fruit.*—None.

*Resistance to frost.*—None.

*Resistance to diseases.*—Very good.

I claim:

1. A new and distinct variety of Grandiflora rose plant characterized by the following combination of characteristics:

(a) exhibits an erect growth habit, (b) forms fully double pure white blossoms which generally are borne one per stem and are long lasting on or off the plant, (c) forms vigorous vegetation, and (d) exhibits very good resistance to diseases, substantially as herein shown and described, together with the parts thereof.

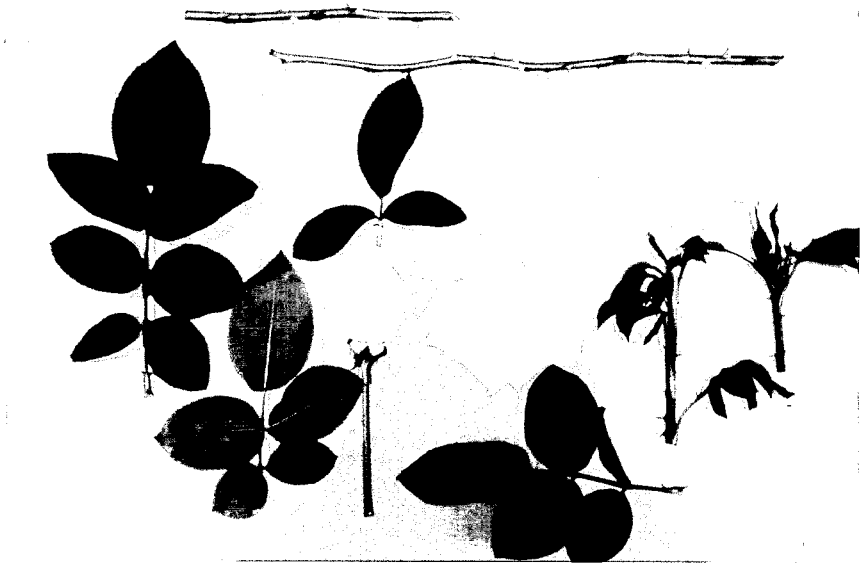

* * * * *